(12) United States Patent
Cai et al.

(10) Patent No.: US 10,335,427 B2
(45) Date of Patent: Jul. 2, 2019

(54) TUMOR PREVENTION AND TREATMENT DRUG AND APPLICATIONS THEREOF

(71) Applicant: Jianping Cai, Beijing (CN)

(72) Inventors: Jianping Cai, Beijing (CN); Zhenhe Wang, Beijing (CN); Jin Li, Beijing (CN); Yunxuan Li, Beijing (CN); Ping Jiang, Beijing (CN); Ju Cui, Beijing (CN)

(73) Assignee: Jianping Cai, Beijing (CN)

( * ) Notice: Subject to any disclaimer, the term of this patent is extended or adjusted under 35 U.S.C. 154(b) by 0 days.

(21) Appl. No.: 16/060,412

(22) PCT Filed: May 16, 2017

(86) PCT No.: PCT/CN2017/084571
§ 371 (c)(1),
(2) Date: Jun. 7, 2018

(87) PCT Pub. No.: WO2018/000975
PCT Pub. Date: Jan. 4, 2018

(65) Prior Publication Data
US 2018/0360863 A1    Dec. 20, 2018

(30) Foreign Application Priority Data
Jun. 29, 2016  (CN) .......................... 2016 1 0491656

(51) Int. Cl.
*A61K 31/708*    (2006.01)
*A61P 35/04*    (2006.01)
*A61P 35/00*    (2006.01)
*A61P 35/02*    (2006.01)

(52) U.S. Cl.
CPC ............ *A61K 31/708* (2013.01); *A61P 35/00* (2018.01); *A61P 35/02* (2018.01); *A61P 35/04* (2018.01)

(58) Field of Classification Search
None
See application file for complete search history.

(56) References Cited

U.S. PATENT DOCUMENTS

2013/0316352 A1* 11/2013 Li .................... C12Q 1/6869
435/6.12

FOREIGN PATENT DOCUMENTS

WO    2005020885 A2    3/2005

OTHER PUBLICATIONS

State Intellectual Property Office of the People's Republic of China (ISR/CN), "International Search Report for PCT/CN2017/084571", China, dated Aug. 24, 2017.
State Intellectual Property Office of the People's Republic of China (ISR/CN), "Written Opinion of the International Searching Authority for PCT/CN2017/084571", China, dated Aug. 24, 2017.
Yizhen Yin et al., Effects of 8-halo-7-deaza-2'-deoxyguansine triphosphate on DNA synthesis by DNA polymerase and cell proliferation, Bioorganic & Medicinal Chemistry, Jun. 18, 2016, pp. 3856-3861, and see abstract, vol. 24, No. 16, ISSN: 0968-0896.

* cited by examiner

*Primary Examiner* — Traviss C McIntosh, III
(74) *Attorney, Agent, or Firm* — Shuang Chang; PSK Intellectual Property Group, LLC

(57) ABSTRACT

The present invention discloses a medicament for the prevention and treatment of tumors, in particular relating to the use of 8-oxo-deoxyguanosine triphosphate (8-oxo-dGTP) in the manufacturing of a medicament for the prevention and treatment of tumors, and a medicament comprising 8-oxo-dGTP for the prevention and treatment of tumors, and falls within the pharmaceutical field. The 8-oxo-dGTP can be used in the manufacturing of a medicament for at least one of the treatment, prevention and control of tumors. The 8-oxo-dGTP has a significant inhibitory effect on tumorigenesis and tumor cell proliferation for many types of tumors, and can serve as a new candidate medicament for the prevention and treatment of tumors. Animal experiments show that the 8-oxo-dGTP is significantly superior to 5-FU in terms of tumor inhibition, therefore has a good industrial availability and great business and social values.

7 Claims, 1 Drawing Sheet

TUMOR PREVENTION AND TREATMENT DRUG AND APPLICATIONS THEREOF

CROSS-REFERENCE TO RELATED APPLICATIONS

This application is a U.S. national phase application of PCT Patent Application Serial No. PCT/CN2017/084571, filed on May 16, 2017, and claims priority to and benefit of Chinese Patent Application No. 201610491656.7, filed on Jun. 29, 2016 in the State Intellectual Property Office of P.R. China, which are incorporated herein by reference in their entireties.

FIELD OF THE INVENTION

The present invention relates to a medicament for the prevention and treatment of tumors, in particular to the use of 8-oxo-deoxyguanosine triphosphate (8-oxo-dGTP) in the manufacturing of a medicament for the treatment, prevention and/or control of tumors, and a medicament comprising 8-oxo-dGTP for the prevention and treatment of tumors, and falls within the pharmaceutical field.

BACKGROUND OF THE INVENTION

The 8-oxo-deoxyguanosine triphosphate (8-oxo-dGTP or 8-oxodGTP) is a nucleotide that is capable of triggering DNA mutations in vivo. Either during normal metabolic activity or under exogenous stimuli, cells will produce a large amount of reactive oxygen species and oxygen-derived free radicals, wherein —OH is highly reactive and can damage biological macromolecules such as carbohydrates, nucleic acids, lipids and amino acids. In nucleic acids, more than 20 kinds of oxidized bases have been detected, among which guanine has the lowest oxidation potential and the C atom at position 8 is the most easily oxidized by hydroxyl radicals to generate 8-oxo-guanosine (8-oxoG), and therefore, 8-oxoG is the most abundant oxidized base in the cell and plays a key role in influencing the stability of genetic information. Reactive oxygen species and oxygen-derived free radicals cause DNA oxidative damage mainly in the following two ways: one is where the guanine in the DNA strand is directly oxidized into 8-oxo-guanosine (8-oxoG); the other is where deoxyguanosine triphosphate (dGTP) in the pool of nucleotides is oxidized into 8-oxo-deoxyguanosine triphosphate (8-oxo-dGTP). 8-oxodG can be mismatched with adenine (A), and the efficiency of the mismatching is almost equivalent to that of the match with cytosine (C), resulting in the base transversion of A: T→G: C, which is the theoretical basis of DNA mutations caused by reactive oxygen species.

No research on the role of 8-oxo-dGTP in the prevention of tumorigenesis and against tumors has been reported either at home or abroad.

SUMMARY OF THE INVENTION

The first technical problem to be solved by the present invention is to provide the use of 8-oxo-deoxyguanosine triphosphate for the manufacturing of a medicament for the treatment, prevention and/or control of tumors.

The second technical problem to be solved by the present invention is to provide a medicament comprising 8-oxo-deoxyguanosine triphosphate for the treatment, prevention and/or control of tumors.

The third technical problem to be solved by the present invention is to provide a method for the treatment, prevention and/or control of tumors.

In order to achieve the objects mentioned above, the present invention utilizes the following technical solutions:

8-oxo-deoxyguanosine triphosphate (8-oxo-dGTP) can be used in the manufacturing of a medicament for the treatment, prevention and/or control of tumors, wherein the treatment, prevention and/or control of tumors refers to one or several uses of inhibiting the proliferation of tumor cells, preventing tumorigenesis, or promoting the death of tumor cells.

The present invention can treat, prevent and/or control tumors by administering one or more anti-tumor medicaments alone or in combination with other therapeutic agents.

The tumors are solid tumors and hematological tumors. The tumors include nervous system tumors, head and neck cancer, nasopharyngeal cancer, oral cancer, thyroid cancer, breast cancer, cervical cancer, endometrial cancer, ovarian cancer, lung cancer, esophageal cancer, stomach cancer, colorectal cancer, liver cancer, pancreatic cancer, bladder cancer, kidney cancer, testicular cancer, prostate cancer, bone tumors, hematological tumors, and lymphomas; and advanced malignancies, unresectable malignancies, metastatic malignancies, etc.

Organisms have a sophisticated ability for clearing oxidized nucleotides. The MutT protein found in *Escherichia coli* (*E. coli*) has the ability to hydrolyze 8-oxodGTP into 8-oxodGMP, thereby preventing 8-oxodGTP from being incorporated into DNA strands at the replicational level. The spontaneous mutation rate of the *E. coli* MutT-deficient strain is significantly increased compared to that of the wild-type strain. Compared with *E. coli*, mammalian cells have a more sophisticated mechanism which is involved in the clearance of oxidized nucleotides from the pool of nucleotide precursors, including MTH1, MTH2, NUDT5, MTH3, etc., all of which are homologous proteins with MutT. When mammalian MTH1, i.e., MutT homolog protein 1, is expressed in MutT-*E. coli*, the spontaneous mutation rate of *E. coli* significantly decreases, thus indicating that these mammalian homolog proteins function similarly to MutT in clearing oxidized nucleotides from the pool of nucleotides.

In 2001, Japanese scientists Sekiguchi, M. et al. constructed MTH1-knockout mice, which were dissected after feeding for 18 months. It was found that the incidence rate of tumors in MTH1−/−mice was significantly higher than that in wild-type mice, with the tumors mainly being concentrated in lung, liver, stomach, etc. In 2014, Swedish scientists Thomas Helleday et al. introduced MTH1 small interfering RNAs (siRNAs) into tumor cells and normal cells, respectively, and found that the survival rate of tumor cells decreased, while that of normal cells showed no significant changes. Their studies with the MTH1 inhibitors TH287 and TH588 further demonstrated that the inhibition of MTH1 expression in tumor cells may selectively kill tumor cells. In addition, nude mice transplantation experiments with melanomas, SW480 colorectal cancer and MCF7 breast cancer also had therapeutic effects on the treatment of TH588. MTH1 is considered to be a new target for tumor therapy.

We hypothesized that the reason why tumor cells can be killed by MTH1 protein inhibition is that the inhibition of the MTH1 protein caused a decrease in the body's ability to clear 8-oxodGTP, and led to elevated levels of 8-oxodGTP, such that a wide range of gene mutations caused thereby had a killing effect on the tumor cells. Based on this assumption, the present study constructed MTH1-knockout mice, as well as tumor xenograft nude mice. By means of increasing the 8-oxodGTP levels in the systemic DNA of model mice via tail vein injection, the effect of 8-oxodGTP on tumorigenesis and proliferation was examined, and the incidence rates of tumors in both MTH1-knockout mice and wild-type mice and the tumor growth rate in tumor xenograft nude mice were observed. Our research results showed that, compared with control groups, MTH1-knockout mice and wild-type mice showed a reduced incidence rate of tumor growth in the 8-oxodGTP group, and the nude mice showed decreased tumor growth. Therefore, this suggests that 8-oxodGTP has an inhibitory effect on tumorigenesis and proliferation.

A medicament for the treatment, prevention and/or control of tumors is provided, said medicament comprising 8-oxo-deoxyguanosine triphosphate (8-oxo-dGTP).

The medicament further comprises a biologically acceptable excipient or carrier.

The medicament is a preparation which is administered orally, by parenteral injection, via nasal mucosa, transdermally, or rectally; or is a depot preparation.

The preparation administered orally is a tablet, a capsule, a flat capsule, a soft capsule, a solution or a suspension; the preparation administered by parenteral injection is a preparation for rapid intravenous injection or continuous infusion; the preparation administered via nasal mucosa is an aerosol, a spray, a mist or a drip agent; the preparation administered transdermally is a gel, an ointment, a sustained release transdermal preparation, a liposomal preparation, a transdermal patch or a transdermal spray; the preparation administered rectally is a suppository or a retention enema; and the depot preparation is a subcutaneously or intramuscularly implanted preparation, or an intramuscularly injected preparation.

A method for the treatment, prevention and/or control of tumors is provided, said method comprising administering, to a mammal, a therapeutically effective dose of 8-oxo-deoxyguanosine triphosphate (8-oxo-dGTP). The therapeutically effective dose is 5 μg-2000 μg/kg of body weight, preferably 200-1000 μg/kg of body weight. The tumors include nervous system tumors, head and neck cancer, nasopharyngeal cancer, oral cancer, thyroid cancer, breast cancer, cervical cancer, endometrial cancer, ovarian cancer, lung cancer, esophageal cancer, stomach cancer, colorectal cancer, liver cancer, pancreatic cancer, bladder cancer, kidney cancer, testicular cancer, prostate cancer, bone tumors, hematological tumors, and lymphomas; and advanced malignancies, unresectable malignancies, metastatic malignancies, etc. This therapeutic method can also be used in conjunction with other conventional methods of treating cancers, such as radiotherapy or surgery.

The advantages of the present invention is as follow: the present invention has unexpectedly found that the 8-oxo-deoxyguanosine triphosphate (8-oxo-dGTP) has a significant inhibitory effect on tumorigenesis and tumor cell proliferation for many types of tumors, and can serve as a new candidate medicament for the prevention and treatment of tumors. Animal experiments show that 8-oxo-deoxyguanosine triphosphate (8-oxo-dGTP) is significantly superior to 5-FU in terms of tumor inhibition, and therefore has good clinical utility and social value.

The present invention is further described in detail below with reference to the accompanying drawings and specific embodiments, which are not to be considered as limiting the present invention. All equivalent substitutions made according to the disclosure of the present invention fall with the scope of protection of the present invention.

DETAILED DESCRIPTION OF THE INVENTION

Embodiment 1: Medicaments Comprising 8-Oxo-dGTP

I. Experimental Materials

Figure 1:
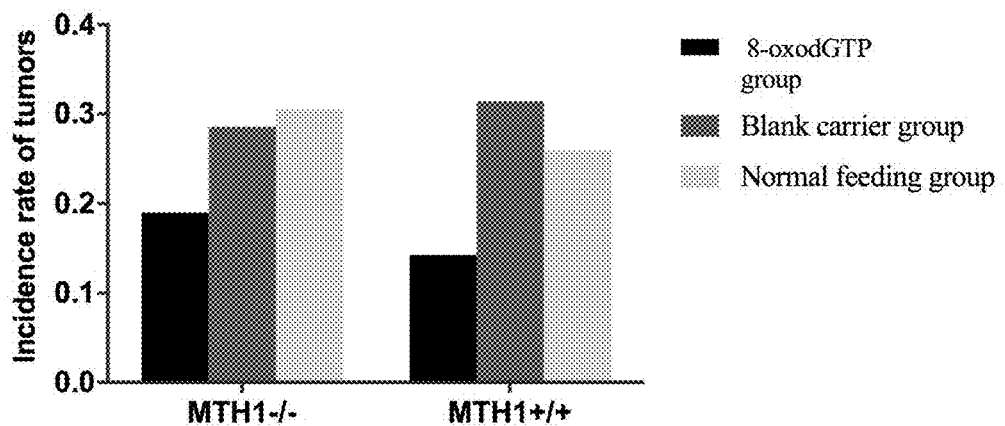
FIG. 1 shows the incidence rates of tumors in MTH1-knockout mice and wild-type mice in Embodiment 2.

1. Active ingredient: 8-oxo-deoxyguanosine triphosphate (8-oxo-dGTP), purchased from Trilink, USA
2. Drug carrier: Entranster™-in vivo reagent of Engreen Biosystem Co., Ltd., Cat. No. 18668-11, Size: 1 ml, purchased from Engreen Biosystem Co., Ltd., Beijing, China II. Preparation Method According to the instruction manual of the drug carrier, the active ingredient and the drug carrier are configured to be a transfection compound with the concentration of the active ingredient, i.e. 8-oxo-deoxyguanosine triphosphate (8-oxo-dGTP), being 0.5 μg/μl, thus obtaining the medicament of the present invention.

Embodiment 2: Animal Experiments for Tumor Prevention and Treatment

I. Experimental Materials

1. Experimental Reagents:
(1) 8-oxodGTP injection: the medicament obtained in Embodiment 1.
(2) Blank carrier reagent: a carrier solution free of the active ingredient, which was obtained by formulating Entranster™-in vivo reagent of Engreen Biosystem Co., Ltd. following the method in Embodiment 1, with pure water replacing 8-oxo-deoxyguanosine triphosphate (8-oxo-dGTP).
(3) 5-fluorouracil (5-FU), a positive control reagent, purchased from Jinyao Amino Acid Co., Ltd., Tianjin, China.
2. Experimental Animals:
(1) MTH1-knockout mice and littermate wild-type mice (the earlier stage was completed in collaboration with Nanjing Model Animal Center, China)
(2) Balb/c nude mice, 18-20 g, 8 weeks, purchased from Huafukang Biotechnology Company, Beijing, China All the mice involved in the experiments were raised according to the specific pathogen free (SPF) animal feeding standards with the indoor temperature controlled at 20° C.-26° C., a humidity of 50%-60%, and alternative lighting of 12 h of light/12 h of dark. The mice were fed with a sterile standard diet, having access to food and water.

3. Experimental Cells:
Hela cells, purchased from ATCC.

II. Experimental Methods

1. Oxidation Induction and Anatomy of MTH1-Knockout Mice

MTH1-knockout mice (MTH1$^{-/-}$) and wild-type mice (MTH1$^{+/+}$) were normally raised for three months, and same were grouped into the 8-oxodGTP group, the blank carrier group and the normal feeding group, and same were subjected to tail vein injection of 8-oxodGTP at a dose of 500 μg/kg/time, once every 10 days, for a total of 50 times. The mice were dissected under aseptic conditions, and all the organs of the mice were carefully screened, and the incidence of tumors in each group was observed and recorded.

2. Inoculation, Oxidation Induction and Anatomy of Nude Mice

5×10⁶ Hela cells (200 μl) were inoculated subcutaneously into the armpit of nude mice. After growing to a certain size, the tumor mass was reinoculated subcutaneously into the armpit of 24 nude mice, which were then randomly grouped into the 5-FU positive control group, the blank carrier control group, and the 8-oxodGTP group, and on the second day after the second inoculation, these nude mice were dosed intravenously. The 5-FU group was injected at a dose of 15 mg/kg/time, the 8-oxodGTP group was injected at a dose of 500 μg/kg/time, and the carrier control group was injected at an equal volume of blank carrier reagents. The injections were performed twice every week, for a total of 10 times. After the injections, the tumor mass was taken and weighed, so as to calculate the inhibition rate (inhibition rate=(1-T experimental group/C control group)×100%).

III. Experimental Results

1. Reduction of the Incidence Rate of Tumor in Mice by 8-oxodGTP

As shown in Table 1 and FIG. 1, the incidence rates of tumors decreased in MTH1-knockout mice and wild-type mice after tail vein injection of 8-oxodGTP, compared with the blank carrier group and the normal feeding group. Table 2 shows mice tumor types and the quantity of each group.

TABLE 1

Incidence rates of tumors in MTH1 knockout mice and wild-type mice.

| Group | 8-oxodGTP group | Blank carrier group | Normal feeding group |
|---|---|---|---|
| MTH1⁻/⁻ | 19.00% | 28.57% | 30.56% |
| MTH⁺/⁺ | 14.29% | 31.43% | 26.00% |

TABLE 2

Tumor types and quantity of MTH1 knockout mice and wild-type mice.

| | Quantity of tumors (%) | | | | | |
|---|---|---|---|---|---|---|
| | 8-oxodGTP group | | Blank carrier group | | Normal feeding group | |
| Type of tumors | -/- | +/+ | -/- | +/+ | -/- | +/+ |
| MTH1 | | | | | | |
| Intestinal tumor | 1 (3) | 0 (0) | 3 (11) | 3 (9) | 1 (3) | 7 (21) |
| Mesenteric tumor | 4 (13) | 2 (6) | 0 (0) | 2 (6) | 4 (11) | 3 (9) |
| Retroperitoneal tumor | 3 (10) | 0 (0) | 2 (7) | 2 (6) | 3 (8) | 0 (0) |
| Gastric tumor | 0 (0) | 0 (0) | 0 (0) | 1 (3) | 0 (0) | 0 (0) |
| Liver tumor | 1 (3) | 0 (0) | 1 (4) | 3 (9) | 3 (8) | 1 (3) |
| Lung tumor | 1 (3) | 0 (0) | 1 (4) | 1 (3) | 1 (3) | 0 (0) |
| Kidney tumor | 0 (0) | 0 (0) | 1 (4) | 0 (0) | 1 (3) | 0 (0) |
| Adrenal tumor | 0 (0) | 0 (0) | 0 (0) | 0 (0) | 0 (0) | 0 (0) |
| Neck tumor | 2 (6) | 2 (6) | 0 (0) | 0 (0) | 2 (6) | 0 (0) |
| Pancreatic tumor | 0 (0) | 0 (0) | 0 (0) | 0 (0) | 1 (3) | 0 (0) |
| Meditastinal tumor | 4 (13) | 0 (0) | 0 (0) | 2 (6) | 1 (3) | 0 (0) |
| Sum | 6 (19%) | 5 (14%) | 8 (29%) | 11 (31%) | 11 (31%) | 9 (26%) |
| Number of mice | 36 | 34 | 28 | 35 | 36 | 34 |

2. Inhibition of Tumor Mass Growth in Nude Mice by 8-oxodGTP

Figure 2:
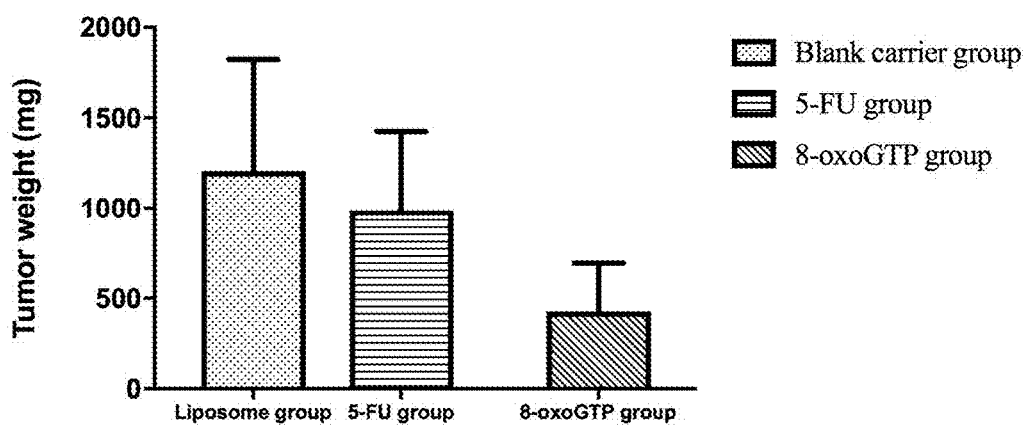
FIG. 2 shows the tumor weight of nude mice in Embodiment 2.

As shown in Table 3 and FIG. 2, compared to the blank carrier group, the 5-FU group showed an inhibition rate on tumor growth of 18%, whereas the 8-oxodGTP group showed an inhibition rate on tumor growth of 65%.

TABLE 3

Tumor weight and inhibition rate in nude mice.

| Group | Tumor weight (mg) | Inhibition rate |
|---|---|---|
| Blank carrier group | 1206 ± 616.87 | 0% |
| 5-FU group | 988 ± 436.94 | 18% |
| 8-oxodGTP group | 428 ± 266.12 | 65% |

IV. Experimental Conclusions

After tail vein injection with 8-oxo-dGTP, MTH1-knockout mice and wild-type mice showed a reduced incidence rate of tumors, and nude mice showed decreased tumor growth, indicating that 8-oxo-dGTP may play an inhibitory role in tumorigenesis and proliferation.

Although the embodiments of the present invention have been shown and described above, it should be understood that the above embodiments are merely exemplary and should not be construed as limiting the present invention. A person skilled in the art may make changes, modifications, replacements and variations to the above embodiments within the scope of the present invention as long as same do not depart from the principles and objectives of the present invention. These changes, modifications, replacements and variations all belong to the scope of protection of the present invention.

What is claimed is:

1. A method for at least one of the treatment and control of tumors, comprising the following steps of:
   Step 1, preparing a medicament by mixing a biologically acceptable excipient or a carrier with 8-oxo-deoxyguanosine triphosphate (8-oxo-dGTP) to obtain a therapeutically effective dose of 8-oxo-dGTP; and Step 2, administration, to a mammal, the medicament containing the therapeutically effective dose of 8-oxo-dGTP.

2. The method according to claim 1, wherein at least one of the treatment and control of tumors refers to one or more uses for inhibiting the proliferation of tumor cells, preventing tumorigenesis, or promoting the death of tumor cells.

3. The method according to claim 1, wherein the tumors are solid tumors and hematological tumors.

4. The method according to claim 3, wherein the tumors are nervous system tumors, head and neck cancer, nasopharyngeal cancer, oral cancer, thyroid cancer, breast cancer, cervical cancer, endometrial cancer, ovarian cancer, lung cancer, esophageal cancer, stomach cancer, colorectal cancer, liver cancer, pancreatic cancer, bladder cancer, kidney cancer, testicular cancer, prostate cancer, bone tumors, hematological tumors, and lymphomas; advanced malignancies, unresectable malignancies, and metastatic malignancies.

5. The method according to claim 1, wherein the administration is by oral, by parenteral injection, via nasal mucosa, by transdermal, or by rectal; or by a depot preparation.

6. The method according to claim 5, wherein the administration by oral is by a tablet, a capsule, a flat capsule, a soft capsule, a solution or a suspension; the administration by parenteral injection is by a preparation for rapid intravenous injection or continuous infusion; the administration via nasal mucosa is by an aerosol, a spray, a mist or a drip agent; the administration by transdermal is by a gel, an ointment, a sustained release transdermal preparation, a liposomal preparation, a transdermal patch or a transdermal spray; the administration by rectal is a suppository or a retention enema; and the depot preparation is a subcutaneously or intramuscularly implanted preparation, or an intramuscularly injected preparation.

7. The method according to claim 1, wherein the therapeutically effective dose is 5 µg-2000 µg/kg of body weight, preferably 200-1000 µg/kg of body weight.

* * * * *